United States Patent
Kim et al.

(10) Patent No.: US 10,488,301 B2
(45) Date of Patent: Nov. 26, 2019

(54) JIG FOR STRENGTH TEST OF SIDE DOOR OF MOTOR VEHICLE

(71) Applicant: MS AUTOTECH, Gyeongsangbuk-do (KR)

(72) Inventors: Woo Yeong Kim, Gyeonggi-do (KR); Won Ik Eom, Gyeonggi-do (KR); Young Sun Choi, Gyeonggi-do (KR); Hyun Woo Lee, Gyeonggi-do (KR)

(73) Assignee: MS AUTOTECH, Gyeongsangbuk-do (KR)

( * ) Notice: Subject to any disclaimer, the term of this patent is extended or adjusted under 35 U.S.C. 154(b) by 287 days.

(21) Appl. No.: 15/480,117

(22) Filed: Apr. 5, 2017

(65) Prior Publication Data
US 2018/0292295 A1   Oct. 11, 2018

(51) Int. Cl.
*B23Q 3/00* (2006.01)
*G01M 17/007* (2006.01)
*G01N 3/30* (2006.01)
*G01N 3/04* (2006.01)

(52) U.S. Cl.
CPC .......... *G01M 17/0078* (2013.01); *G01N 3/04* (2013.01); *G01N 3/30* (2013.01); *G01N 2203/001* (2013.01); *G01N 2203/0447* (2013.01)

(58) Field of Classification Search
USPC .................. 269/296, 297, 298, 299
See application file for complete search history.

(56) References Cited

U.S. PATENT DOCUMENTS

| | | | | |
|---|---|---|---|---|
| 4,538,044 | A | * 8/1985 | Kadowaki | B23K 37/047 219/79 |
| 4,767,046 | A | * 8/1988 | Kumagai | B05B 13/0285 228/4.1 |
| 5,374,799 | A | * 12/1994 | Nishimoto | B62D 65/02 219/117.1 |
| 2013/0145616 | A1 | * 6/2013 | Jang | B62D 65/026 29/822 |

* cited by examiner

*Primary Examiner* — Joseph J Hail
*Assistant Examiner* — Shantese L McDonald
(74) *Attorney, Agent, or Firm* — IP & T Group LLP

(57) ABSTRACT

A jig for strength test of a side door of a motor vehicle for supporting a side outer component product includes a jig frame, a first roof rail jig unit installed in an upper rear end of the jig frame and configured to support a roof rail of an upper end portion of a center pillar of a product, a second roof rail jig unit installed in an upper central portion of the jig frame and configured to support a roof rail of the center pillar of the product, a cowl crossbar jig unit installed in a front upper end of the jig frame and configured to support a front roof and a hinge portion of the product, and a plurality of side seal jig units installed in a lower end portion of the jig frame and configured to support a lower end portion of the product.

5 Claims, 5 Drawing Sheets

JIG FOR STRENGTH TEST OF SIDE DOOR OF MOTOR VEHICLE

TECHNICAL FIELD

The present invention relates to a jig used when testing the strength of a side door of a motor vehicle and, more particularly, to a jig for strength test of a side door of a motor vehicle capable of facilitating a mounting and demounting work of a side door through the change of positions of bolt fastening portions and capable of being generally used for different types of motor vehicles through the adoption of a guide pin and a sliding structure.

BACKGROUND ART

Vehicle safety tests include a front collision test in which the entire front portion of a motor vehicle is collided with a wall, a front overlap test in which a part of the front portion of a motor vehicle is collided with a hard wall or a steel bar structure, and a side collision test in which the side surface of a motor vehicle is collided.

The side collision test is performed to measure the safety at the time of side collision and is conducted by causing a wall body moving at a predetermined speed to collide with the side surface of a motor vehicle.

It is desirable that the side collision test is performed with respect to an actual motor vehicle. However, in a process of developing a new car, it is necessary to conduct tests for different designs. Thus, it is often the case that the tests are performed using a side outer component which is a test-purpose chassis to which a side door can be fastened.

The side outer component is used for a side collision test in a state in which the side outer component is coupled to a jig for strength test of a side door. The side outer component is formed in different structures depending on the types of motor vehicles.

Thus, side outer components conforming to the sizes and positions of bodies of different motor vehicles and jigs for supporting the side outer components need to be manufactured in order to perform a strength test for a side door. This poses a problem in that the cost of development of a new car increases.

Furthermore, in the prior art, counting bolts are fastened in order to fix a product. Thereafter, the flange portion of the product and the jigs are welded to each other. This poses a problem in that the welded portions have to be separated when demounting the product after a test.

SUMMARY OF THE INVENTION

In view of the aforementioned problems inherent in the related art, it is an object of the present invention to provide a jig for strength test of a side door of a motor vehicle, which is capable of reducing the cost incurred when manufacturing different jigs for a strength test for each vehicle type.

Another object of the present invention is to provide a jig for strength test of a side door of a motor vehicle, which is configured to enable a support portion to move in a longitudinal direction and a transverse direction of a jig frame when fixing a side outer component product corresponding to a side door frame of a motor vehicle, and which is capable of being generally used regardless of a vehicle type.

According to one embodiment of the present invention, there is provided a jig for strength test of a side door of a motor vehicle for supporting a side outer component product corresponding to a side door frame of a motor vehicle in order to perform a side collision test, including: a jig frame; a first roof rail jig unit installed in an upper rear end of the jig frame and configured to support a roof rail of an upper end portion of a center pillar of a product; a second roof rail jig unit installed in an upper central portion of the jig frame and configured to support a roof rail of the center pillar of the product; a cowl crossbar jig unit installed in a front upper end of the jig frame and configured to support a front roof and a hinge portion of the product; and a plurality of side seal jig units installed in a lower end portion of the jig frame and configured to support a lower end portion of the product, wherein each of the first roof rail jig unit and the second roof rail jig unit includes a linear motion guide portion movable in a longitudinal direction of the jig frame in conformity with the size of the product and a guide pin portion movable in a transverse direction of the jig frame, and the cowl crossbar jig unit includes a guide pin portion movable in the longitudinal direction of the jig frame.

In the jig, each of the first roof rail jig unit and the second roof rail jig unit may be configured so that the linear motion guide portion is positioned on the side of the product and the guide pin portion is positioned on the side of the jig frame.

In the jig, the cowl crossbar jig unit may include a cowl crossbar configured to support a front end roof of the product, a hinge coupling piece to which an upper end of a hinge portion of the product is coupled, and a jig body formed in a bracket shape so that the cowl crossbar is coupled to an upper surface of the jig body and the hinge coupling piece is coupled to one side surface of the jig body, the guide pin portion provided on the side of the jig frame in the jig body.

In the jig, a rear surface of the cowl crossbar may be removably coupled to the jig body by bolts.

In the jig, each of the side seal jig units may include a jig body provided, on an upper side of one end thereof, with a groove into which a lower end flange surface of the product is inserted, and fixed at the other end thereof to the jig frame, and a reinforcing plate installed on an upper surface of the jig body so as to prevent deformation of the jig body.

In the jig, each of the side seal jig units may be configured to support the product so that a predetermined gap is maintained between a lower end of an impact plate and a lower end of the product.

With the jig for strength test of a side door of a motor vehicle according to the present invention, a sliding structure composed of a linear motion guide and a guide pin forming part are adopted in each jig unit which supports a side outer component product corresponding to a side door frame of a motor vehicle.

Thus, the jig can be generally used regardless of the product standard. This provides an effect that there is no need to manufacture different jigs for each vehicle type.

Furthermore, it is possible to use a door support unit structure disposed in a position similar to the position in an actual vehicle. This provides an effect that it is possible to enhance the reliability of a test result.

Moreover, each jig unit making contact with a product, specifically a cowl crossbar jig unit, is configured to support both a cowl crossbar and an upper end of a hinge coupling portion. This provides an effect that the structure of the jig is simplified and the manufacturing cost is reduced.

In addition, bolt fastening portions are formed so as to avoid product contact portions. This provides an effect that it is possible to shorten the time required for mounting and demounting a product.

MODE FOR CARRYING OUT THE INVENTION

A preferred embodiment of a jig for strength test of a side door of a motor vehicle according to the present invention will now be described in detail with reference to the accompanying drawings.

Figure 1:
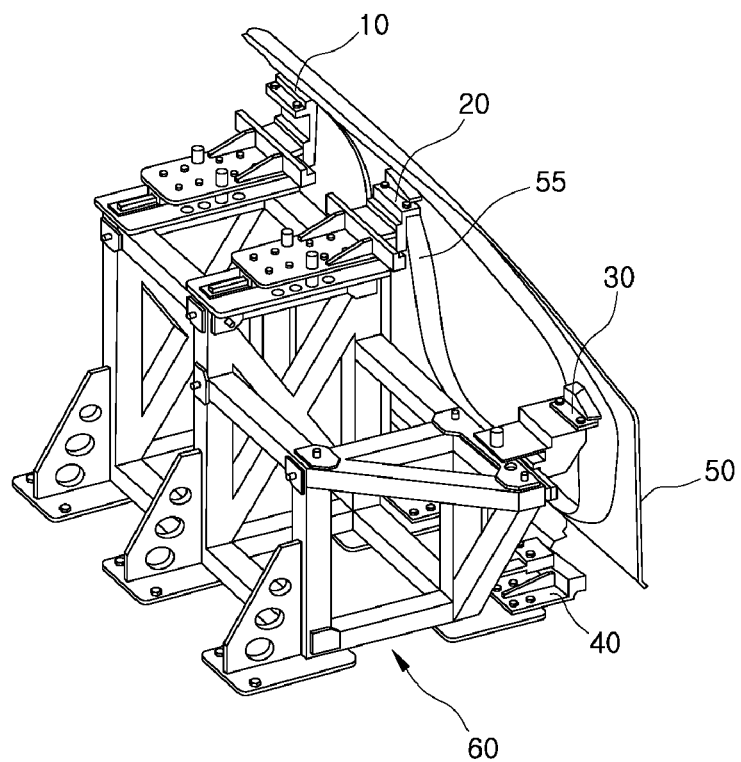
FIG. 1 is a perspective view showing a view showing a jig for strength test of a side door of a motor vehicle according to the present invention.
Figure 1:
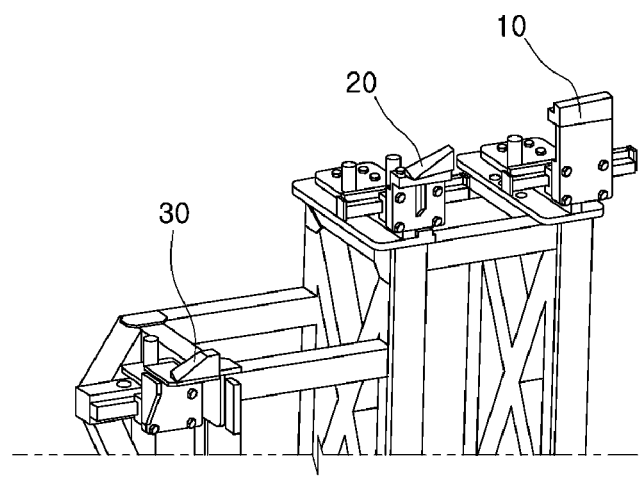
Figure 2:
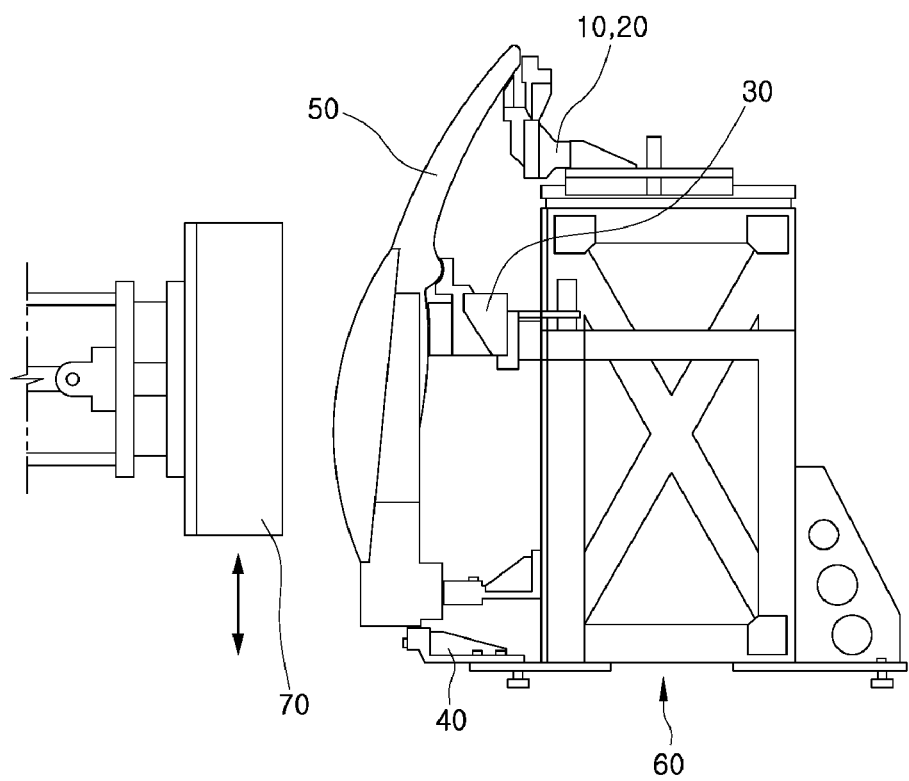
FIG. 2 is a side view of the jig for strength test of a side door of a motor vehicle according to the present invention.
Figure 3:
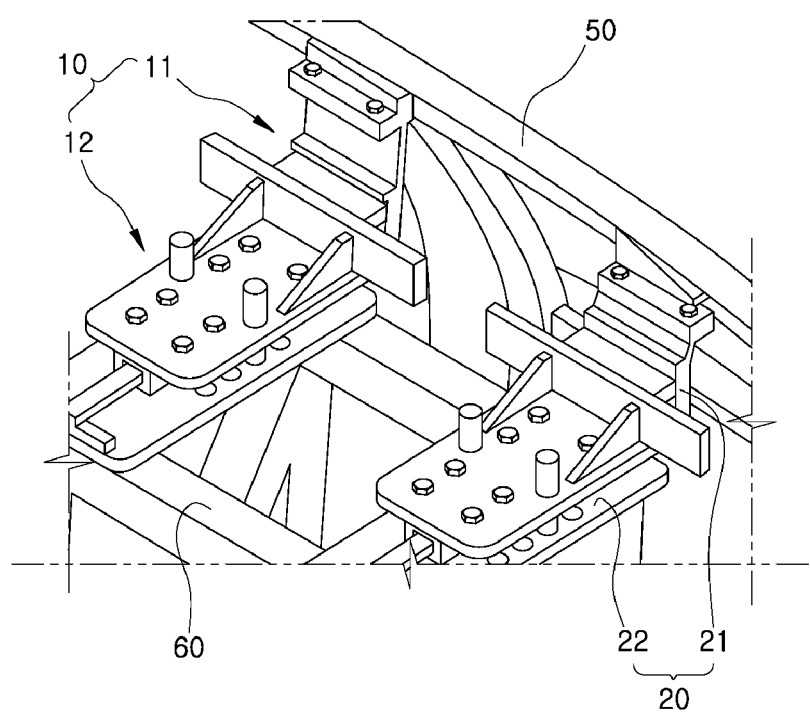
FIG. 3 is an enlarged view showing a first roof rail jig unit and a second roof rail jig unit which are major parts of the jig for strength test of a side door of a motor vehicle according to the present invention.
Figure 4:
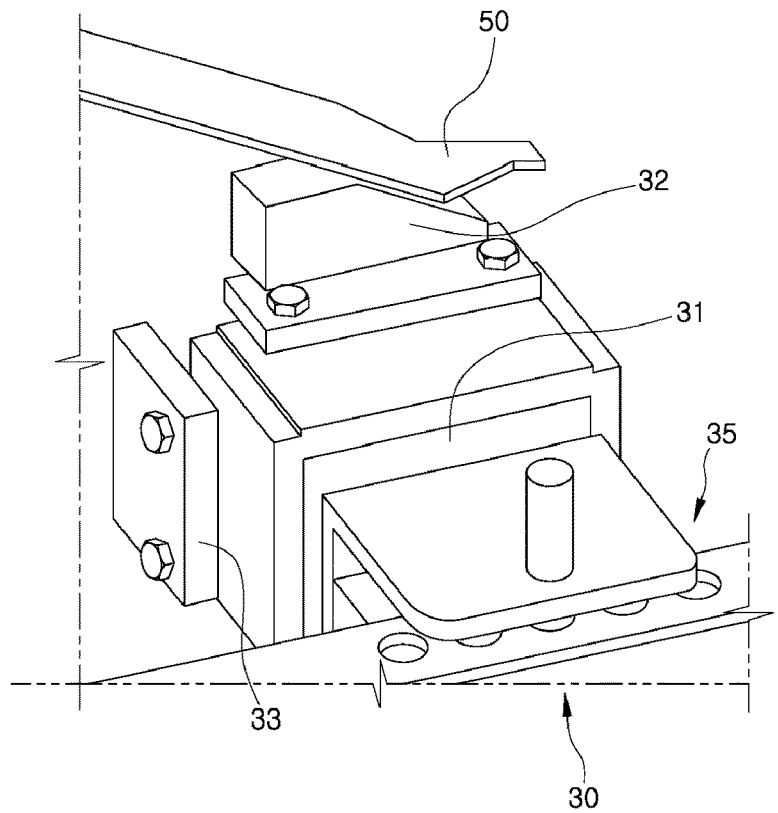
FIG. 4 is an enlarged view of a cowl crossbar jig unit which is a major part of the jig for strength test of a side door of a motor vehicle according to the present invention.
Figure 5:
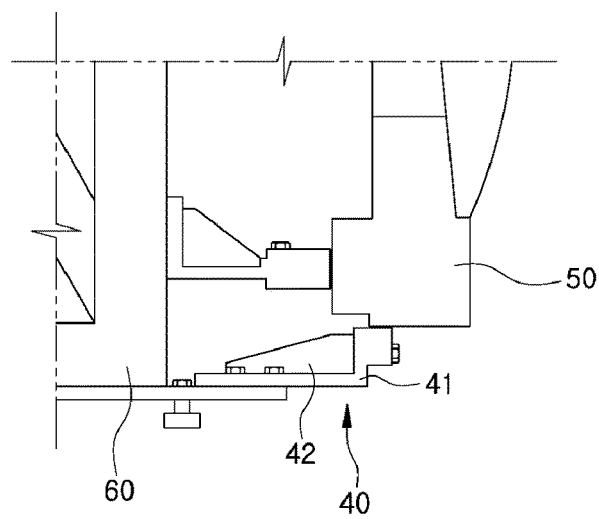
FIG. 5 is a reference view showing a screw fastening portion of a cowl crossbar which is a major part of the jig for strength test of a side door of a motor vehicle according to the present invention.
Figure 6:
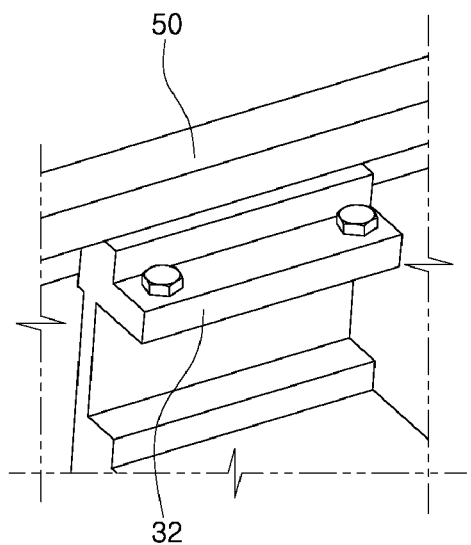
FIG. 6 is an enlarged view of a side seal jig unit which is a major part of the jig for strength test of a side door of a motor vehicle according to the present invention.

Referring to FIGS. 1 to 6, the jig for strength test of a side door of a motor vehicle according to the present invention is configured to support a side outer component product corresponding to a side door frame of a motor vehicle in order to perform a side collision test.

The jig for strength test of a side door of a motor vehicle includes: a jig frame 60; a first roof rail jig unit 10 installed in an upper rear end of the jig frame 60 and configured to support a roof rail of an upper end portion of a center pillar 55 of a product 50; a second roof rail jig unit 20 installed in an upper central portion of the jig frame 60 and configured to support a roof rail of the center pillar 55 of the product 50; a cowl crossbar jig unit 30 installed in a front upper end of the jig frame 60 and configured to support a front roof and a hinge portion of the product 50; and a plurality of side seal jig units 40 installed in a lower end portion of the jig frame 60 and configured to support a lower end portion of the product 50.

In this regard, each of the first roof rail jig unit 10 and the second roof rail jig unit 20 includes a linear motion guide portion 11 or 21 movable in a longitudinal direction of the jig frame 60 in conformity with the size of the product 50 and a guide pin portion 12 or 22 movable in a transverse direction of the jig frame 60. The cowl crossbar jig unit 30 includes a guide pin portion 35 movable in the longitudinal direction of the jig frame 60.

Each of the first roof rail jig unit 10 and the second roof rail jig unit 20 is configured so that the linear motion guide portion 11 or 21 is positioned on the side of the product 50 and the guide pin portion 12 or 22 is positioned on the side of the jig frame 60.

The linear motion guide portion 11 or 21 includes a guide rail provided on the side of the jig frame 60 and a guide block provided on the side of a door frame so as to move along the guide rail.

Since the linear motion guide portion 11 or 21 is provided in each of the first roof rail jig unit 10 and the second roof rail jig unit 20, the product 50 may be caused to horizontally move along the longitudinal direction of the jig frame 60.

Furthermore, since the guide pin portion 12 or 22 is provided in each of the first roof rail jig unit 10 and the second roof rail jig unit 20, the product 50 may be caused to move in the transverse direction of the jig frame 60.

As a result, the jig for strength test of a side door of a motor vehicle can be generally used regardless of the size of the product 50 that varies depending on the vehicle type.

The cowl crossbar jig unit 30 includes a cowl crossbar 32 configured to support a front end roof of the product 50, a hinge coupling piece 33 to which an upper end of a hinge portion of the product 50 is coupled, and a jig body 31 formed in a bracket shape so that the cowl crossbar 32 is coupled to an upper surface of the jig body 31 and the hinge coupling piece 33 is coupled to one side surface of the jig body 31, the guide pin portion 35 provided on the side of the jig frame 60 in the jig body 31.

It is preferred that the rear surface of the cowl crossbar 32 is removably coupled to the jig body 31 by bolts. As a result, it is possible to prevent the bolt coupling portion from interfering with the contact portion between the cowl crossbar 32 and the product 50. Thus, the product can be mounted and demounted with ease and the time required for mounting and demounting the product 50 can be shortened.

Each of the side seal jig units 40 includes a jig body provided on an upper side of one end thereof with a groove into which a lower end flange surface of the product 50 is inserted, and fixed at the other end thereof to the jig frame 60, and a reinforcing plate 42 installed on an upper surface of the jig body 41 so as to prevent deformation of the jig body 41.

Each of the side seal jig units 40 is configured to support the product 50 so that a gap between a lower end of an impact plate 70 and a lower end of the product 50 is 127 mm or more according to the standard FMVSS 214.

The side seal jig units 40 may support the lower end of the product 50 at different heights. This makes it possible to change the inclination angle of the product 50.

In the present jig for strength test of a side door of a motor vehicle configured as above, the parts of the jig to be fixed to the side outer component product 50 can be moved in the longitudinal direction and the transverse direction of the jig frame 60. In addition, the angle of the product can be changed. Therefore, the present jig can be generally used in different types of motor vehicles.

That is to say, in the first roof rail jig unit 10 and the second roof rail jig unit 20 which support the upper end of the side outer component product, the linear motion guide portion 11 or 21 can support the part to be fixed to the product 50 so that the part can be moved in the longitudinal direction of the jig frame 60.

Furthermore, the guide pin portion 12 or 22 can support the part to be fixed to the product 50 so that the part can be moved in the transverse direction of the jig frame 60.

In the cowl crossbar jig unit 30 which supports the front upper end of the product 50, the guide pin portion 35 can support the part to be fixed to the product 50 so that the part can be moved in the longitudinal direction of the jig frame 60.

In addition, the side seal jig units 40 can support the product 50 at different heights in conformity with the angle of the lower end of the product 50.

According to the present jig described above, the positions of the parts of the respective jig units to be fixed to the product can be changed in a corresponding relationship with the structure of the product that corresponds to the side door frame of a motor vehicle. Thus, the present jig can be generally used regardless of the vehicle type.

While a preferred embodiment of the present invention has been described above, the present invention is not limited to this embodiment. It is to be understood that various changes and modifications may be made without departing from the scope of the invention defined in the claims.

What is claimed is:

1. A jig for strength test of a side door of a motor vehicle for supporting a side outer component product corresponding to a side door frame of a motor vehicle in order to perform a side collision test, comprising:
   a jig frame;
   a first roof rail jig unit installed in an upper rear end of the jig frame and configured to support a roof rail of an upper end portion of a center pillar of a product;
   a second roof rail jig unit installed in an upper central portion of the jig frame and configured to support a roof rail of the center pillar of the product;
   a cowl crossbar jig unit installed in a front upper end of the jig frame and configured to support a front roof and a hinge portion of the product; and
   a plurality of side seal jig units installed in a lower end portion of the jig frame and configured to support a lower end portion of the product,
   wherein each of the first roof rail jig unit and the second roof rail jig unit includes a linear motion guide portion movable in a longitudinal direction of the jig frame in conformity with the size of the product and a guide pin portion movable in a transverse direction of the jig frame, and
   the cowl crossbar jig unit includes a guide pin portion movable in the longitudinal direction of the jig frame,
   and wherein each of the first roof rail jig unit and the second roof rail jig unit is configured so that the linear motion guide portion is positioned on the side of the product and the guide pin portion is positioned on the side of the jig frame.

2. The jig of claim 1, wherein the cowl crossbar jig unit includes a cowl crossbar configured to support a front end roof of the product, a hinge coupling piece to which an upper end of a hinge portion of the product is coupled, and a jig body formed in a bracket shape so that the cowl crossbar is coupled to an upper surface of the jig body and the hinge coupling piece is coupled to one side surface of the jig body, the guide pin portion provided on the side of the jig frame in the jig body.

3. The jig of claim 2, wherein a rear surface of the cowl crossbar is removably coupled to the jig body by bolts.

4. The jig of claim 1, wherein each of the side seal jig units includes a jig body provided, on an upper side of one end thereof, with a groove into which a lower end flange surface of the product is inserted, and fixed at the other end thereof to the jig frame, and a reinforcing plate installed on an upper surface of the jig body so as to prevent deformation of the jig body.

5. The jig of claim 4, wherein each of the side seal jig units is configured to support the product so that a predetermined gap is maintained between a lower end of an impact plate and a lower end of the product.

* * * * *